United States Patent [19]

Giese

[11] Patent Number: 4,656,252

[45] Date of Patent: Apr. 7, 1987

[54] AMIDOBIOTIN COMPOUNDS USEFUL IN A AVIDIN-BIOTIN MULTIPLE LAYERING PROCESS

[76] Inventor: Roger W. Giese, 56 Oakland Ave., Quincy, Mass. 02170

[21] Appl. No.: 616,851

[22] Filed: Jun. 4, 1984

Related U.S. Application Data

[63] Continuation-in-part of Ser. No. 532,036, Sep. 14, 1983, Pat. No. 4,478,914, which is a continuation of Ser. No. 272,297, Jun. 10, 1981, abandoned, which is a continuation-in-part of Ser. No. 114,898, Jan. 24, 1980, Pat. No. 4,282,287.

[51] Int. Cl.$^4$ .................. C07K 17/06; C12N 11/06; C07D 495/04
[52] U.S. Cl. ................... 530/350; 530/402; 530/810; 530/812; 530/816; 548/303; 435/7; 435/6; 435/28; 435/177; 455/181; 455/188; 455/21
[58] Field of Search .................. 435/7, 21, 6, 28, 177, 435/181, 188, 814; 260/112 R; 548/303

[56] References Cited

U.S. PATENT DOCUMENTS 4,228,237 10/1980 Hevey et al. .................. 435/7
4,230,797 10/1980 Boguslaski et al. .................. 435/7
4,298,685 11/1981 Parikh et al. .................. 435/188

OTHER PUBLICATIONS

Costello et al., *Clin. Chem.* 25(9) 1979, pp. 1572-1580, Enhancement of Immune Cellular . . . Avidin-Biotin System.
Guesdon et al., *J. of Histochem. and Cytochem.* 27(8), 1979, pp. 1131-1139, Use of Avidin-Biotin . . . Techniques.

*Primary Examiner*—John Kight
*Assistant Examiner*—Garnette D. Draper
*Attorney, Agent, or Firm*—Weingarten, Schurgin, Gagnebin & Hayes

[57] ABSTRACT

Amidobiotin extender compounds useful, for example, in avidin-biotin multiple-layering process, which compounds include caproylamidobiotin-NHS ester, caproylamidobiotin-horse radish peroxidase, caproylamidobiotinribonuclease and caproylamidobiotin-alkaline phosphatase (B-ALP).

9 Claims, 2 Drawing Figures

LAYERED SURFACE

AMIDOBIOTIN COMPOUNDS USEFUL IN A AVIDIN-BIOTIN MULTIPLE LAYERING PROCESS

REFERENCE TO PRIOR APPLICATIONS

This application is a continuation-in-part of U.S. patent application Ser. No. 532,036, filed Sept. 14, 1983, now U.S. Pat. No. 4,478,914 which patent application is a continuation of U.S. patent application Ser. No. 272,297, filed June 10, 1981, now abandoned, and which patent application is a continuation-in-part of patent application Ser. No. 114,898, filed Jan 24, 1980, now U.S. Pat. No. 4,282,287, issued Aug. 4, 1981, all of which are hereby incorporated by reference.

BACKGROUND OF THE INVENTION

Avidin is a protein found in egg whites and contains four subunits. Biotin is a stable, water-soluble vitamin. Biotin and avidin interact specifically under mild and certain harsh conditions to form a strong, stable, avidin-biotin complex in which each of the four subunits of avidin bind a biotin molecule. This binding persists when biotin is attached by means of its carboxyl group to another molecule. For example, biotin may be secured or attached to molecules on the surface of a cell or to anticellular antibodies which have been reacted onto a cell, and then subsequently is reacted with a ferritin-avidin conjugate, to provide a method for localization studies in affinity cytochemistry (see, for example, *Trends in Biochemical Science*, 3, N257 (1978), hereby incorporated by reference). Biotinyl-antibody and conjugated avidin products (with fluorescein, rhodamine, ferritin or horse radish perosidase) are offered commercially, to provide investigators with reagents for studying biochemical and immunochemical structures or processes; for example, the location or extent of a cell-surface substances.

A modified avidin-biotin system has been employed to enhance immune cellular agglutination of erythrocytes (see *Clinical Chemistry*, 25, No. 9, 1572 (1979), hereby incorporated by reference). Biotin or caproylamidobiotin was either attached directly to the cells or indirectly using biotin or caproylamidobiotin-anticellular antibody. The addition of avidin then achieved agglutination, and a biotin or caproylamidobiotin-conjugated macromolecule was added as an extender in conjunction with more avidin, to enhance the agglutination.

SUMMARY OF THE INVENTION

My invention concerns amidobiotin compounds and a method for preparing such compounds and relates to a process of preparing a multiple-layer system ("layering") and to the multiple layer system so prepared using such compounds. In particular, my invention concerns a process of preparing a multiple-layer system involving repetitive, specific, molecular or particulate layers of a proteinaceous material and ligand material, to the multiple-layer system so prepared, and to the use of the system and process to change or modify surface properties.

My multiple-layer process and multiple-layer product comprises a protein such as avidin and a ligand material such as biotin (and any derivatives, analogs or substitutes of these which still comprise an analogous binding interaction) and a material referred to as an extender. An extender is defined as a molecule or substance to which one or more ligands such as biotin have been attached such that these ligands still undergo binding by the protein such as avidin. The extender useful in my invention may comprise those extenders which are described in the Clinical chemistry publication, supra, or other biotin-modified molecules or particles. Typical and specific extenders include, but are not limited to: fibrinogen, albumin, succinylated polylysine and ribonuclease appropriately modified with biotin or biotin derivatives. These extenders may be used separately or in combination or as separate layers of different extenders as desired.

Typical examples of avidin derivatives include, but are not limited to: succinyl avidin, ferritin avidin, enzyme avidin and cross-linked avidin. A typical example of an avidin analog is the bacterial biotin-binding protein, streptavidin, whose physical and chemical characteristics are similar to those of avidin. A typical example of an avidin substitute or other proteins is a ligand-binding substance with multiple ligand-binding sites, such as a lectin, antibody, protein A (purified or cell-bound), etc., in conjunction with an appropriate ligand (lectins bind sugar ligands, antibodies bind hapten or antigenic determinant ligands, and protein A binds $F_c$ ligand). Typical examples of biotin derivatives as ligands include, but are not limited to: caproylamidobiotin and biocytin. Typical examples of biotin analogs are desthiobiotin and biotin sulfone and of biotin substitutes are ligands for appropriate substitute binding substances; that is, sugars, haptens or antigenic determinants, $F_c$, for lectins, antibodies, protein A, etc., as defined above.

The multiple-layer process is defined as the successive, repetitive attachment of the protein and extenders to a surface to build up alternate layers of each. The initial step could be attachment of either one of these reagents (covalently or noncovalently) to a surface, or direct firm attachment of biotins to the surface. For example, where the surface is, firstly, covalently bonded with biotin, then layering would be achieved by repetition of the following sequence of steps (a–d) to build up successive layers of avidin and extender: (a) add avidin; (b) wash away unbound avidin; (c) add extender; and (d) wash away unbound extender, and then, optionally, perform a derivatization reaction; for example, cross-linking or modifying of funtional groups, in between any of the above steps and/or after all the layers have been developed to change the properties further; for example, provide a more complete coverage of the surface, more stability, different functional groups, etc. In my layering process, primarily or exclusively monomolecular or monoparticulate layers of avidin and extender (a single extender or various extender materials may be used in a given multiple-layer process) are built up on a surface, but the process may be relaxed by omitting washing steps, thereby possibly mixing in coverage with multimolecular or multiparticulate species.

Any conceivable surface may be employed, whether biological, nonbiological, organic, inorganic, or a combination of any of these, and whether formulated or existing as molecules, molecular aggregates, particles, strands, precipitates, gels, sheets, tubing, spheres, containers, capillaries, pads, slices, film, etc. (for example, cells, tissue, tumors, organelles, proteins, polymers, elastomers, microorganisms, viruses, nucleic acids, plastics, resins, polysaccharides, silica or silica-based materials, carbon, metals, inorganic salts, chromatographic supports, test tubes, etc.) provided only that some component of the layering system can be attached firmly to initiate the process. The attachment of avidin to biotin or extender can proceed under mild conditions (for example, aqueous solvents and room temperature).

The basic concept of developing repetitive, specific, alternate, monomolecular or monoparticulate layers on a surface is unprecedented. My "layering" system bears no relation to conventional surface-treatment processes, such as painting, because of the latter's gross numbers of molecules and variable layer thickness involved, the poorly controlled nonspecific nature of the process, the complex and often crude nature of many of the components, and the major effect achieved by the first or second layer with subsequent layers typically leading to equivalent or diminished returns.

My "layering" process constitutes a new process at the molecular or monoparticulate level, with an opportunity to develop specifically and to control molecular distances and constructions, with exact choices of components. In my process, the first layer is merely a beginning, and the overall layering process involves a careful and well-defined building up and constructing of an array of molecules or particles on a given surface in an exact and sophisticated manner, and with great variety, if so desired. The process and product are characterized by a unique array of characteristics which requires all of the aspects mentioned (repetitive, specific, alternate monomolecular or monoparticulate layers), and which qualitatively and/or quantitatively can differ vastly from the properties or effects achieved by the intital layer or even initial several layers.

Overall my layering avidin-biotin system offers significant advantages in terms of the overall accessibility, stability, cost, size, solubility and multiple binding sites of its components, and the analogs, derivatives and substitutes for avidin and biotin are within the scope of my layering system.

A wide variety of problems associated with surfaces are now subject to a new mode of attack with my multiple-layer process and product. For example, my process may be used to change the adsorptive, functional, catalytic, reactivity, transport, adhesive, stability, charge, toxicity, biological foreignness, frictional, electrical potential, chromatographic, pore size, rigidity, wettability, reflective, conductance, energy transfer, immunogenic, roughness, hardness, etc. properties of a surface; to stabilize the inherent properties of a surface; to determine distances between sites (for example, once the distance is layered, it is shut off from further layering, or signal molecules, such as a fluorescence molecule and a fluorescence quencher, or interacting spin labels, could be used to reveal when the layers from the sites reach a certain proximity); to establish connections between sites on the same or different surfaces; to cause movement of sites on or between surfaces and, therefore, of the surfaces themselves; to disrupt a surface; to provide an exact distance between functional molecules or substances on a surface or between different surfaces; to create, study, optimize or otherwise change an interaction or binding or disruption between surfaces or between surfaces and some other substances or molecules; to provide a special microenvironment or access or protection, etc. for functional molecules or substances on surfaces; to allow larger or more complex particles to be developed by starting with a core molecule or particle and building up layers; and to allow the development of exceedingly small circuitry.

Specific examples of some uses would be to increase the extent of attachment of an enzyme, antibody, coenzyme, fluorophor, radionuclide, drug or other special atom or molecule to a surface for enhancing immunoassay, affinity chromatography, therapy, enzyme engineering, solar-energy conversion, catalysis, etc.; to reduce the pore sizes of a dialysis or filtration surface; to change retention characteristics; to change the pore size and/or surface properties of silica or silica-based particles for chromatographic or adsorption-control purposes; to exert or to enhance a physical, chemical or biological activating, inhibiting, disrupting, toxicity or killing action against a desirable or undesirable surface, such as a tumor cell, infectious microorganism, diseased tissue or disease-causing agent; to change the foreignness (for example, immunogenicity) of host tissue for reduced rejection by donor or decreased graft-vs.-host response in tissue-transplant procedures; to reduce or eliminate the foreignness of artificial tissue or implant materials (for example, reduced thrombogentic action, reduced immune or phagocytic response) in artificial-organ or -tissue operations (for example, involving plastics and other polymers, etc.); to constitute a glue or adhesive for joining tissues to other tissues or artificial surfaces; to fix tissues; to preserve foods; to use in or achieve molecular surgery; to create channels or reservoirs for reactive molecules or products; to bring together drugs, enzymes, energy-transport molecules, etc. into an arrangement and structure which optimizes their performance and action; and to create novel physiological-transport agents. Other uses of my multiple-layer process and product would be apparent to a person skilled in the art.

My invention concerns a novel class of amidobiotin compounds useful in the layering process and in other systems for clinical assay techniques. My amidobiotin compounds are useful as biotin-extender materials to attach covalently biotin to a substance and to improve the binding of proteinaceous material such as avidin to biotin. The amidobiotin-extender compounds comprise biotin, biotin derivatives, biotin analogs, and biotin substitutes having a reactive carboxylic group covalently bonded through an amido group to an amino carboxylic acid and the carboxylic group of the amino acid covalently reacted to a hydroxy group of a cyclic compound such as N-hydroxysuccinimide (NHS) or to the reactive amino group of macromolecules such as an enzyme such as ribonuclease, amino- horse radish peroxidase or alkaline phosphatase (B-ALP). The general formula of the amidobiotin compounds of the invention comprise:

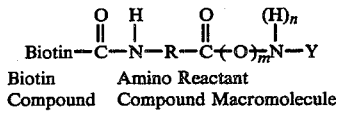

Biotin Compound    Amino Reactant Compound    Macromolecule where R is a spacer group to separate the biotin from the macromolecule and potential steric hindrance. Typically R may be an aryl group such as a phenylene group or alkyl substituted phenylene radical, an alicyclic group such as a $C_5$ or $C_6$ group or preferably an alkyl group such as a $C_1$–$C_{12}$ or more such as a $C_3$–$C_{10}$ polymethylene group. Y is a reactive amino or hydroxyamino compound such as a proteinaceous material containing reactive amino groups such as an enzyme like amino- horse radish peroxidase or ribonuclease or may be a hydroxyamino-containing group such as heterocyclic nitrogen-containing hydroxy substituted 5 or 6 membered heterocyclic group such as a N-hydroxysuccinimide. The integer n or m may be 0 or 1 depending on whether the amino reactant Y is a primary or secondary or hydroxy amine. Typical novel compounds would comprise, but not be limited to: benzoyl amidobiotin-N-hydroxysuccinimide; $C_1$–$C_{12}$ alkanoyl amidobiotin-N-hydroxysuccinimide; for example, caproylamidobiotin-NHS; $C_1$–$C_{12}$ alkanoyl amidobiotin-horse radish peroxidase; for example, a caproylamidobiotin-HRPO; and a $C_1$–$C_{12}$ alkanoyl amidobiotin-ribonuclease; for example, a caproylamidobiotin-ribonuclease and alkanoyl amidobiotin-alkaline phosphatase; for example, caproylamidobiotin-alkaline phosphatase (B-ALP).

The covalently-reactive amidobiotin compounds are prepared by reacting an amino carboxylic acid with the biotin generally in the presence of an activator compound such as carbodiimide or carbonyldiimidazole to activate the carboxylic group of the biotin for reaction with the amino group of the amino acid, followed by activation of the carboxyl group of the attached amino carboxylic acid. While biotin may be employed, it is preferred to react the amino acid with commercially available biotin-NHS, since biotin-NHS is a more stable intermediate and purification of the resulting amidobiotin-NHS compound is enhanced. The amino acid compound used in the preparation has one reactive primary amino group at or near one end and one carboxylic acid group at or near the other end of the molecule with a spacing group of intermediates such as a $C_1C_{12}$ hydrocarbon group. Preferably amino carboxylic acid would include amino alkanoic acids such as epsilon amino caproic acid and delta amino valeric acid, and similar intermediate and long chain ($C_1$–$C_{12}$, such as $C_3$–$C_8$) amino fatty acids.

Caproylamidobiotin-NHS, a novel substance is synthesized as follows:

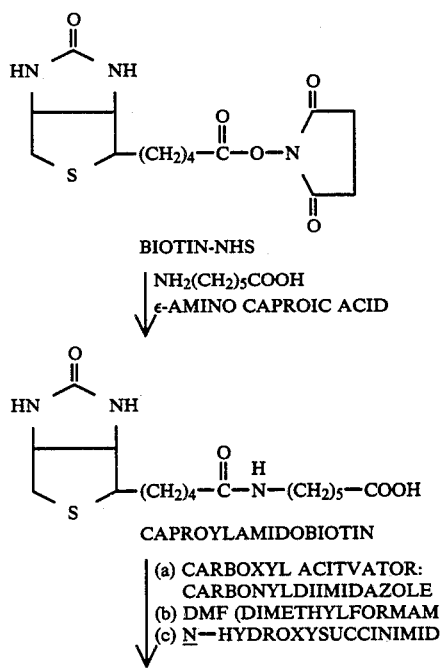

CAPROYLAMIDOBIOTIN-NHS

In the preparation of the compound, biotin-NHS is first reacted with $\epsilon$-amino caproic acid to give caproylamidobiotin. This latter substance is next activated at its carboxyl group by carbonyldiimidazole, so that it can be covalently coupled with N-hydroxysuccinimide forming caproylamidobiotin-NHS. By furnishing a reactive, extended form of biotin, this compound allows the biotin group to be covalently attached to other substances possessing reactive amino groups. The subsequent caproylamidobiotin substances thereby can undergo avidin binding onto their extended biotin residues.

Caproylamidobiotin-horse radish peroxidase (biotinyl-HRPO) a novel substance, is synthesized as follows:

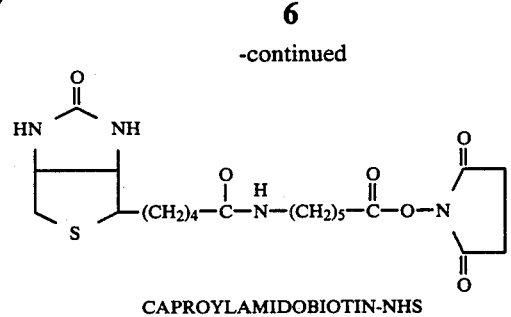

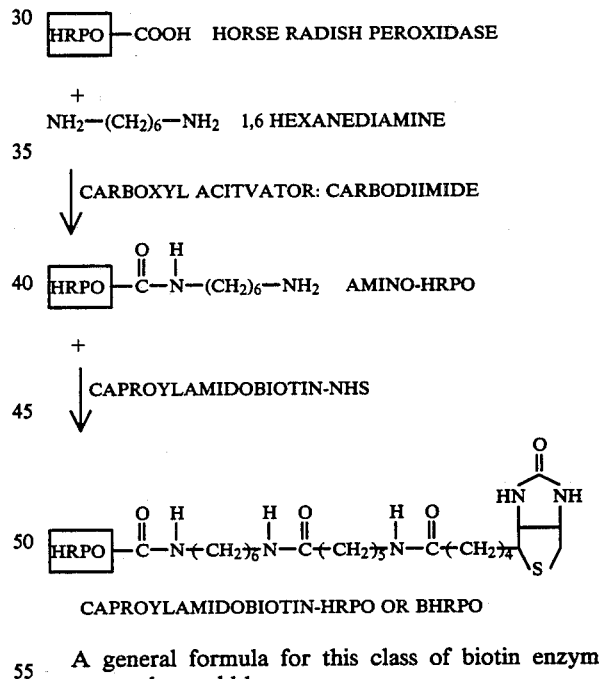

CAPROYLAMIDOBIOTIN-HRPO OR BHRPO

A general formula for this class of biotin enzyme compounds would be:

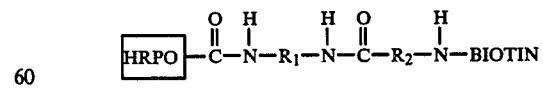

where $R_1$ is an alkyl radical of $C_2$–$C_{12}$ and $R_2$ is an alkyl radical of $C_1$–$C_{12}$. $R_1$ is derived from alkyl diamine reaction with HRPO, while $R_2$ is derived from a selected amino carboxylic acid.

Initially the carboxyl groups on this enzyme are activated with the water soluble carbodiimide reagent, EDC, so that they can be covalently coupled to a diamine such as an alkyl diamine like 1,6-hexanediamine. This affords a horse radish peroxidase derivative having extended amino groups that can react readily with caproylamidobiotin-NHS leading to caproylamidobiotin-horse radish peroxidase. This latter novel substance, possessing biotin residues while also maintaining its enzymatic activity, is a useful signal extender for noncovalent binding to avidin.

Caproylamidobiotin-ribonuclease, a novel substance is synthesized as follows:

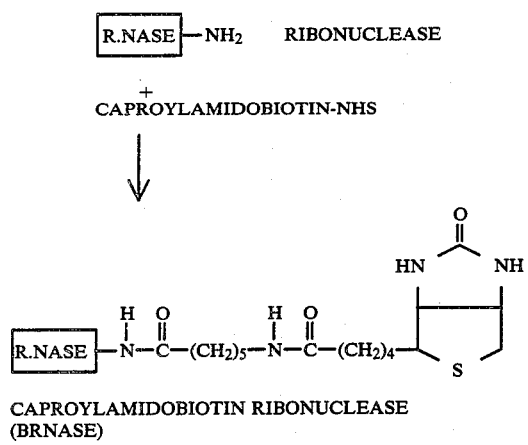

CAPROYLAMIDOBIOTIN RIBONUCLEASE
(BRNASE)

Ribonuclease inherently possessing reactive amino groups is reacted with caproylamidobiotin-NHS leading to the formation of caproylamidobiotin-ribonuclease. Characterization of this latter substance, based on its reaction with trinitrobenzenesulfonic acid, shows an incorporation of nearly seven biotin molecules per mole of enzyme. The average number of these that are avidin reactive, based on an assay with 2-(4'-hydroxyazobenzene)- benzoic acid, is 1.6. Also caproylamidobiotin-alkaline phosphatase (B-ALP) can be prepared in a similar manner employing alkaline phosphatase which contains reactive amino groups as the enzyme starting material These substances are therefore useful as an extender for layering with avidin.

My layering system will be demonstrated employing the process with certain caproylamidobiotin ribonuclease found particularly to be effective as an extender. An appropriate model surface and signal extender are used to demonstrate my layering process. Essentially, nonadsorbing conditions for all reagents were achieved in order to avoid nonspecific effects. An aminoethylpolyacrylamide as a surface material and a signal extender were used; that is, horse radish peroxidase modified successively with hexanediamine/carbodiimide, caproylamidobiotin NHS and succinic anhydride.

My process includes not only the basic layering process, but also "amplification layering", to achieve relatively increasing amounts of corresponding substances in successive layers during this process. Such amplification layering is essential for many of the potential benefits and opportunities of layering to be realized fully. For example, a general, basic problem with surface treatments involving coatings of one to several molecules is that complete coverages are not achieved. An amplification-layering process can provide complete surface coverage, because of its ability to continue to expand the surface coating in all available directions.

For the purpose of illustration only, my multiple-layer process and product will be described with reference to certain specific embodiments; however, it is recognized that those persons skilled in the art may make certain changes and modifications, all within the scope and intent of my invention.

DESCRIPTION OF THE EMBODIMENTS

Figure 1:
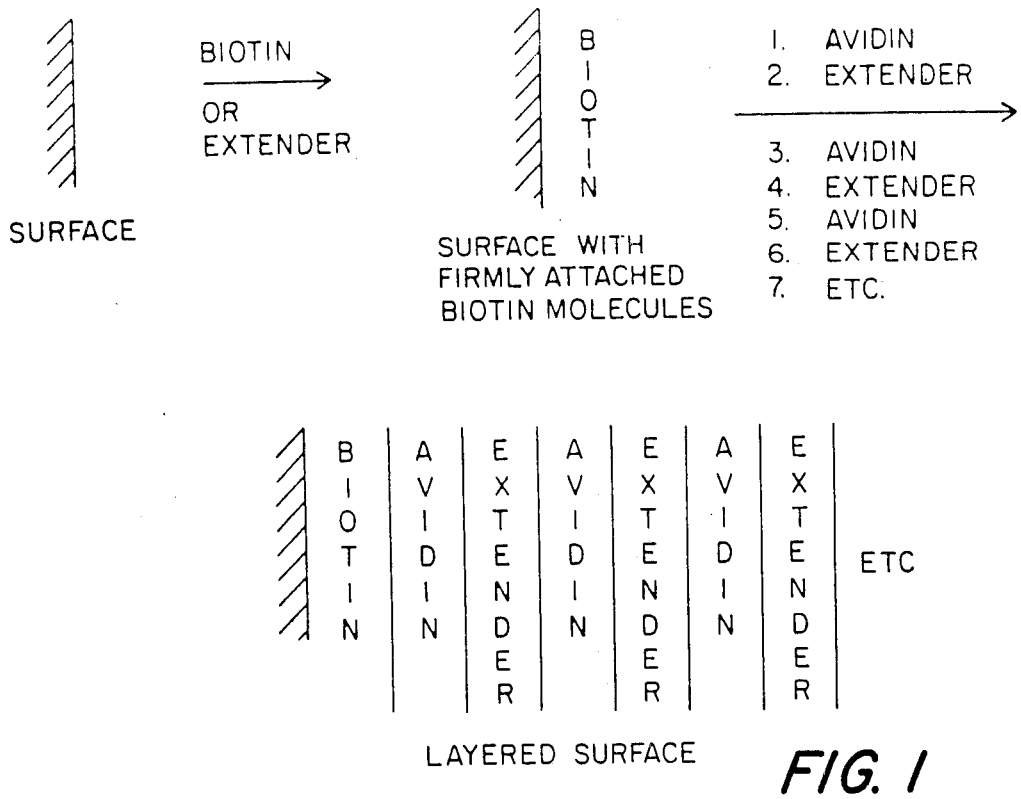
FIG. 1 is a schematic illustration of the multiple-layer process and layering system of my invention.

FIG. 1 is a schematic illustration of a multiple-layer process and layering system of my invention, wherein the biotin is covalently bonded directly to the illustrative surface in the first step, avidin is applied in the next step, and extender (a material to which biotin groups are attached as defined previously) is added, followed by repetitive further additions of avidin and noncovalent extender with intermediate washing steps to remove excess reagents.

It is recognized that the layers may be mixed, that various extenders and forms of avidin (and any derivatives, analogs or substitutes of these) may be used separately, concurrently, intermittently, etc. in a given layering process, that the layering process may result in constant, increasing or decreasing amounts of corresponding substances in successive layers, and that the layers may proceed in the form of molecular and/or particulate sheets, clumps, spheres, patches, rods, tubes, etc. from the initiation sites on the surface.

Figure 2:
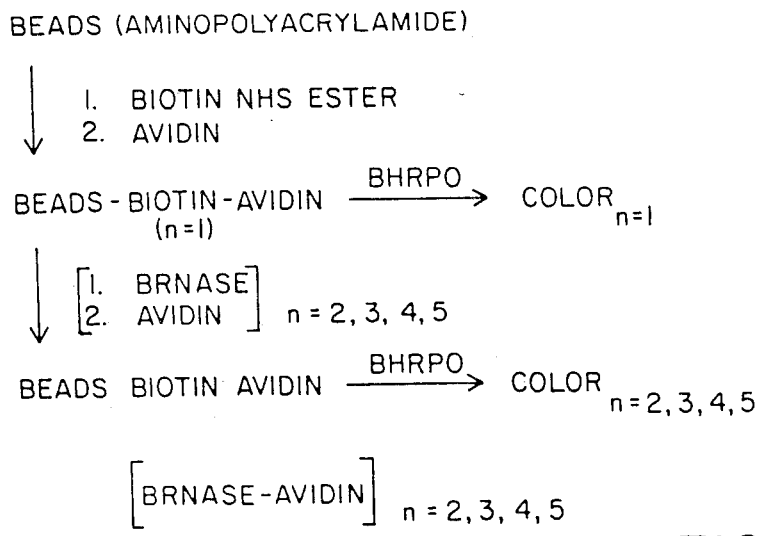
FIG. 2 is a schematic illustration of a specific multiple-layer process and layering system of my invention.

FIG. 2 shows a schematic illustration of a specific, multiple-layer process and product, wherein the surface comprises polyacrylamide particles containing reactive alkylamine groups, which then was modified by reaction with a layer of biotin-NHS esters. The modified surface was then coated with alternating successive layers of avidin and a biotin-ribonuclease extender material, illustrated as five successive layers, to modify the surface of the particles. The extent of avidin attachment in each layering step was monitored by adding an aliquot of biotin-horse radish peroxidase (BHRPO) to each avidin layer treatment. The BHRPO served as a signal extender. Appropriate washing and control steps and treatment were carried ou. The HRPO color at 500 nanometers was measured after each avidin layering step as a measure of the amount of avidin (most specifically, available avidin-binding sites for BHRPO), and the layering process was found to generate increasing amounts of avidin with each avidin layer (amplification layering), one of the three possibilities (constant, decreasing or increasing) cited earlier. The color-vs.-number-of-layers data is shown in Table I.

TABLE I

| Absorbance 500 nm (color) vs. Number of Layering Cycles | | |
|---|---|---|
| No. of Layers Avidin (n) | Color Absorbance | Absorbance Difference Values |
| 1 | .746 | |
| | | .086* |
| 2 | .832 | |
| | | .132 |
| 3 | .964 | |
| | | .160 |
| 4 | 1.124 | |
| | | .255 |

TABLE I-continued

Absorbance 500 nm (color) vs. Number of Layering Cycles

| No. of Layers Avidin (n) | Color Absorbance | Absorbance Difference Values |
|---|---|---|
| 5 | 1.379 | |

*0.832− 0.746 = 0.086

In order to illustrate more fully the nature of the invention and the manner of practicing the same, the following Example is presented:

EXAMPLE I

Materials

1. Affigel-701 from Bio-Rad—an aminoethyl derivative of polyacrylamide in a bead form, 1-3 microns in diameter. The beads were provided in an aqueous suspension at 25±3 u/mol of amine groups/ml.
2. Phosphate buffered saline (PBS)—an 0.01M sodium phosphate, 0.15M sodium chloride, pH 7.4.
3. Avidin—dissolved in PBS at 0.1 mg/ml based on weight.
4. Wash buffer—The buffer used for all washing steps was PBS containing bovine serum albumin (BSA) at 0.02% wt and Tween-20 surfactant at 0.05% wt.
5. HRPO substrate—was freshly prepared by dissolving phenol (100 mg) and 4-aminoantipyrine (16.2 mg) in a solution composed of 0.5M $Na_2HPO_4$(2 ml), 0.5M $KH_2PO_4$(18 ml), water (180 ml) and 30% $H_2O_2$(20 ul).
6. Silanized glass tubes—Disposable borosilicate glass tubes (12×75 mm) were silanized by filling with a 2% solution of chlorotrimethylsilane in benzene. The silanizing reagent was decanted after ½ hour, the tubes rinsed with acetone and air-dried.
7. Biotin NHS ester (biotin N-hydroxysuccinimide ester)—was prepared as defined in Jasiewicz, M. M., Schoenberg, D. R., and Mueller, G. C., *Exp. Cell Res.* 100, 213 (1978), hereby incorporated by reference.
8. Caproylamidobiotin-NHS Ester was prepared as follows: Suspend biotin-N-hydroxysuccinimide [340 mg, 1 mmol,] in 3 mL of dry dimethylformamide. To this add 4 mL of aqueous sodium bicarbonate (0.1 mol/L, pH 8.0) containing ε-amino caproic acid (131 mg, 1 mmol). Stir the suspension magnetically for 4 h at room temperature. Most of the solvent can be removed on a rotary evaporator at reduced pressure (with use of a water aspirator). Suspend the moist, oily, white residue in approximatey 10 ml of aqueous citric acid (100 g/L). Collect the suspension on Whatman no. 1 filter paper and wash with cold water five times. Dry the washed precipitate at reduced pressure at 45° C. over $P_2O_5$ for three days. (No attempt to clean or characterize this intermediate further; the average yield assuming pure product, was 87% at this stage.)

Dissolve this intermediate (310 mg, 0.87 mmol) in dry dimethylformamide (20 mL) at 95° C. in a round-bottom flask. While magnetically stirring this solution, add all at once 5mL of dimethylformamide containing carbonyldiimidazole (162 mg, 1 mmol). Maintain the temperature at 95° C. for 30 min, then allow the flask to cool at room temperature. Two hours later, add N-hydroxysuccinimide (100 mg, 0.87 mmol). Seal the flask with Parafilm and stir overnight.

Place the flask on a rotary evaporator, and remove the dimethylformamide at reduced pressure (water aspirator), using a bath temperature of approximately 55° C. Transfer the resulting pale yellow oil to an Erlenmeyer flask with 15 mL of dry 2-propanol. After several hours the flask will contain an off-white solid precipitate. Aspirate the supernate and dissolve the solid with gentle heating in 25 mL of dry 2-propanol. Reduce the volume to approximately 10 mL by gentle boiling, and allow the flask to cool. Very fine white crystals will develop. After removing the supernate by decantation, dry the solid at reduced pressure over $P_2O_5$ at 60° C. overnight. The yield was 240 mg (61%) and the uncorrected melting point was 149°-152° C. (d); the product gave a single spot when checked by thin-layer chromatography.

9. Caproylamidobiotin-ribonuclease (BRNase) was prepared as follows: Dissolve RNase (10 g/L) in phosphate-buffered saline and treat 1-mL aliquots at room temperature with a fresh solution of caproylamidobiotin-N-hydroxysuccinimide ester (approximately a 100-fold molar excess in each case) dimethylformamide. For RNase, 33 mg in 0.4 mL use a control that involves treatment with an equivalent volume of dimethylformamide without the ester.

After immediate manual shaking, rotate the solution for 1 h at room temperature. Dialyze against three changes of phosphate-buffered saline (1 L each) at 4° C. for a total of 48 h. Measure the percentage of amino groups modified with caproylamidobiotin with 2, 4, 6-trinitrobenzenesulfonic acid and assay the avidin binding with 2-(4′-hydroxyazobenzene) benzoic acid.

10. BHRPO (caproylamidobiotin horse radish peroxidase) was prepared as follows: dissolve 10 mg of horse radish peroxidase (Worthington Biochemical) in 1 ml of water. This was added to a solution consisting of 1,6-hexanediamine (116 mg), 0.2M sodium pyrophosphate (2.0 ml), water (5.0 ml) and sufficient concentrated HCl to bring the pH to 5.5. A solid water-soluble carbodiimide, 1-ethyl-3-(3-dimethylaminopropyl) carbodiimide (EDC) was added to the gently mixed solution at room temperature. Three separate additions of 190 mg each were made over a 1-hour period. 1 ½ hours after the first addition, the contents of the beaker were placed in a dialysis bag and dialyzed against 4×400 ml of PBS (pH=7.4). An aliquot (10 ml) from the dialysis bag was added to a solution of caproylamidobiotin-NHS ester (4.1 mg) in N,N-dimethylformamide (DMF) (0.1 ml). This solution was allowed to stand at room temperature for 1 ½ hours and was then dialyzed against 4 X 400 ml of PBS (pH=7.4).

An aliquot (2 ml) of the above was placed in a dialysis bag and dialyzed against $NaHCO_3$ (1M) for 24 hours. The sample (at pH=8.6) was removed from the bag, placed in a small beaker with a magnetic mixer and reacted with 5×10 ul aliquots (15 minutes apart) of succinic anhydride (40 mg) in DMF (1 ml). The sample was placed in a dialysis bag 15 minutes after the last addition and dialyzed against 4×400 ml of PBS (pH=7.4).

Assuming 100% recovery of enzyme, the concentration of biotinyl-HRPO (BHRPO) would be approximately 0.8 mg/ml. It migrated electrophoretically (cellulose acetate, pH 8.6 buffer) in a manner similar to native enzyme (although the band was more diffuse).

11. Caproylamidobiotin-alkaline phosphatase (B-ALP) is prepared as follows: dissolve 10 mg of alkaline phosphatase in 5 ml of phosphate-buffer saline and treating with a fresh solution of caproylamidobiotin-N-hydroxysuccinimide ester (approximately a 100 fold molar excess over the enzyme) in dimethylformamide. After vortexing, rotate the solution for one hour at room temperature and dialyze against three changes of 0.01 M TRIS-Cl buffer, pH 7.5 (1 L each) at 4° C.

12. Biotin-beads suspension—Affigel-701 (5.0 ml, about 125 u mol of amine groups) was added to PBS (5.0 ml). This suspension was vortexed 10 seconds, and biotin NHS ester (43 mg, 125 u mol) dissolved in DMF (0.1 ml) was added all at once. The reaction mixture was allowed to mix end over end for 2 hours at room temperature. The beads were packed by centrifugation and the supernatant discarded. The bead pellet was resuspended in PBS and washed with 4×20 ml of PBS. The beads (biotin beads) were finally suspended in PBS (20 ml) containing NaN$_3$ (0.02%).

Layering of Biotin Beads

Aliquots (50 ul) of biotin-bead suspension (magnetically mixing) were placed in 12×75 mm silanized glass tubes. Each tube was treated with avidin (0.1 mg in 1 ml PBS) for 10 minutes at room temperature. The beads were then centrifuged and the supernatants collected. The beads wre washed X3 with wash buffer.

A layer was applied to the avidin-biotin beads by suspending them in 1 ml of caproylamidobiotin RNase (BRNase approximately 60 ug/ml) for 10 minutes. The beads were then spun and the supernatants collected. The beads were then washed X3 with wash buffer. The newly added biotin residues were next reacted with avidin as above. The sequence of avidin followed by BRNase, with intermittent washing steps, was repeated four more times. This process is set forth in FIG. 2.

Functional biotin binding sites on avidin-biotin beads (or layered beads) were detected by suspending aliquots of the beads after each avidin step in 200 ul of BHRPO (2 ug/ml) in PBS for 30 minutes. Unbound enzyme was removed by threefold washing with wash buffer. Bound enzyme was detected by addition of HRPO substrate (4.5 ml). After 30 minutes at room temperature, the tubes were chilled in an ice bath for 5 minutes and then spun. The supernatants were decanted and diluted with PBS (4.5 ml).

The A$_{500}$ values of the diluted substrate solutions were measured on a Gilford 240 using water as a reference, and are given in Table I. As seen, the amount of functional enzyme on the beads is greater with each cycle of layering, and the rate of increase (given by the difference values) also is increasing significantly as the layering proceeds; for example, the value 0.255 between layers 4 and 5 is 2.96 times greater than the value 0.086 between layers 1 and 2. This demonstrates the usefulness of layering for placing functional enzyme on a surface, increasing the amount of functional enzyme on a surface, and achieving an increasing rate of layering for the enzyme; that is, a relative increase in the amount of enzyme attached with each successive layer.

Avidin and some of the ligand binding proteins which may be employed in the practice of my invention are set forth in Table II.

TABLE II

| | Avidin and Some Other Ligand-binding Proteins | | |
|---|---|---|---|
| Protein | Ligand | Affinity (Ka) | Usual No. of binding sites |
| Lectins | Simple sugars | $10^3$–$10^4$ | 4 |
| | membrane sites | $10^6$–$10^7$ | |
| Protein A (S. aureus) | F$_c$ of IgG | $10^7$ | 4 |

TABLE II-continued

| | Avidin and Some Other Ligand-binding Proteins | | |
|---|---|---|---|
| Protein | Ligand | Affinity (Ka) | Usual No. of binding sites |
| Antibodies | Haptens | $10^5$–$10^{11}$ | 2 |
| | Antigenic determinants | $10^5$–$10^{11}$ | 2 |
| Avidin | Biotin | $10^{15}$ | 4 |
| Streptavidin | Biotin | — | 4 |

EXAMPLE II.

Lectin Layering of Affigel-701 Beads

Materials

1. The affigel-701, PBS, wash buffer, HRPO substrate, silanzied glass tubes, aminohexyl-HRPO, and RNase are the same as cited in Example I (Layering of Biotin Beads). Concanavalin A, mannose-binding lectin, is purchased from Sigma Chem. Co.

2. α-D-Mannose hydrazide is prepared as defined in G. A. Orr and R. R. Rando, *NATURE*, 1978, 272, 722–725, herein incorporated by reference.

3. α-D-Mannose residues are attached to the Affigel-701 beads, aminohexyl-HRPO, and RNase by the same procedure except that the beads are washed free of excess reagents with intermittent centrifugation, whereas dialysis is used for the two proteins. The amino groups on Affigel 701, aminohexyl-HRPO, and RNase are first reacted with aqueous glucose in the presence of sodium borohydride. After removal of excess reagents, aqueous periodic acid oxidation of the attached glucose residues yields aldehydes to which α-D-mannose hydrazide residues are attached by reaction in the presence of sodium borohydride. This affords mannosyl-Affigel 701, mannosyl-HRPO, and mannosyl-RNase, respectively. As before, excess reagents are removed by centrifugation in the case of the Affigel, and by dialysis in the case of mannosyl-HRPO and mannosyl-RNase.

Layering of Mannosyl-Affigel-701 Beads

This layering experiment is conducted the same as in Example I, except that concanavalin A is substituted for avidin, mannosyl-Affigel-701 for biotin beads, mannosyl-HRPO for BHRPO, and mannosyl-RNase for BRNase.

EXAMPLE III

Layering of *Staphylococcal Aureus* Cells Involving Protein A and IgG

Materials

1. PBS is defined in Example I.

2. SA cells (staphylococcal aureus cells) are commercially available, e.g. from the Enzyme Center, Boston, Mass., as "IgGsorb". SA cells contain a large number of protein A molecules on their surfaces; protein A binds to F$_c$ on many types of IgG molecules.

3. Oligomeric IgG (IgG dimers, trimers, etc.) is prepared by reacting dilute, aqueous IgG (e.g. Sigma Chem. Co.) with 1-ethyl-3-(3-dimethylaminopropyl)-carbodimide, then dialyzing the product against PBS, and removing any precipitate by centrifugation.

4. FITC—Protein A is a protein A conjugated with fluoresceneisothiocyanate. This fluorescent molecule is commercially available from Pharmacia Fine Chemicals.

5. Oligomeric protein A is preapred by the same procedure as for oligomeric IgG, except starting with protein A, which is commercially available, e.g. from Pharmacia Fine Chemicals.

Layering of SA Cells

1. The SA cells are suspended in PBS and treated with oligomeric IgG.
2. The SA cells, now coated with oligomeric IgG, are centrifuged, the oligomeric IgG supernatant is removed and saved, and the coated SA cells are washed with PBS and isolated by centrifugation.
3. The IgG coated SA cells are then reacted with one of the following: further SA cells, oligomeric protein A, Protein A, or FITC-protein A.
4. The layered SA cells are washed as before, coated again with oligomeric IgG and washed as before.
5. The sequence of steps 3 and 4 is repeated as many times as desired, generating SA cells which are layered with alternate coatings involving protein A and IgG. The extent of layering can be monitored conveniently whenever FITC-Protein A is reacted onto the IgG-coated surface, since FITC-protein A is fluorescent.

EXAMPLE IV

Antibody Layering of Affigel-701 Beads

Materials

1. The Affigel-701, PBS, wash buffer, HRPO substrate, silanized glass tubes, aminohexyl-HRPO, and RNase are the same as cited in Example I (layering of biotin beads).
2. Fluorodinitrobenzene, dissolved in ethanol, is reacted in aqueous, sodium carbonate buffer with the amino groups on Affigel-701, aminohexyl-HRPO, and RNase, yielding the following DMP (dinitrophenyl) products, respectively: DNP-Affigel-701, DNP-aminohexyl-HRPO, and DNP-RNase. Excess fluorodinitrobenzeen and its hydrolysis products are removed from the DNP-Affigel-701 by centrifugation and washing, and from the DNP-aminohexyl-HRPO and DNP-RNase by dialysis.
3. Anti-DNP anitbody is available commercially from Miles Biochemicals. Monoclonal anti-DNP antibody may also be developed by hybridoma techniques and utilized.

Layering of DNP-Affigel 701 beads

This layering experiment is conducted the same as in Example I, except that anti-DNP antibody is substituted for aviden, DNP-Affigel-701 for biotin beads, DNP-HRPO for BHRPO, and DNP-RNase for BRNASE.

EXAMPLE V

Avidin Layering of Glass Test Tubes

Materials

1. The materials are the same as in Example I, except that biotinyl-aminopropyl-glass test tubes are used in place of the two components, biotin beads and silanized glass tubes.
2. Biotinyl-aminopropyl-glass test tubes are prepared as follows: first the test tubes are reacted with α-aminopropyltriethoxysilane in toluene as described by H.H Weetall and A.M. Filbert (1974) in *Methods in Enzymology* (W. B. Jakoby and M. Wilchek, eds.) 34, p. 59 herein incorporated by reference; then the amino groups on the glass surface are reacted with biotin-NHS dissolved in acetonitrile.

Layering of glass tubes

The procedure is the same as in Example 1 except that no beads are involved, and the centrifugation steps are omitted. Thus, the first step is to treat the test tubes with avidin (0.1 mg in 1 ml PBS) for 10 min at room temperature. The avidin solution is poured out and saved. The test tubes are washed X3 with wash buffer, and treated for 10 min with BRNase. This solution is poured out and saved. The test tubes are washed X3 with wash buffer, the newly added biotin residues are reacted as before with avidin, and so on, according to the steps in Example I. As before, at any step when the last layer is avidin, the amount of reactive biotin on the surface can be determined by reacting the tubes with BHRPO and the, after washing, determining the bound enzyme by added HRPO substrate.

EXAMPLE VI

Avidin Layering of Fibrinogen

Materials

The materials are the same as in Example I, except the Fib-B (biotinated fibrinogen, which is prepared as described by S. M. Costello, R. T. Felix, and R. W. Giese, Clin. Chem. 25 (1979), p. 1572, previously incorporated by reference) replaces the biotin beads.

Layering the Fib-B

The procedure is the same as in Example I, except that Fib-B replaces the biotin beads, and that excess reagents are removed from Fib-B after each layering step by means of, e.g., gel filtration in wash buffer on Sephadex G-100 or with an ultrafiltration membrane (e.g. from Millipore or Amicon) rather than by centrifugation and washing. In the case of the Sephadex G-100 column, the layered Fib-B elutes first from this column, and is concentrated by precipitation with organic solvent, or by lyophilization, as necessary, before the next step.

EXAMPLE VII

Avidin Layering of Dialysis Tubing

Materials

1. Cellulosic dialysis membrane is commercially available, e.g. from VWR.
2. Av-membrane is prepared by reacting the cellulosic dialysis membrane with CNBr dissolved in aqueous sodium carbonate. After a short reaction period (e.g. 5 to 10 min), the activated membrane is washed with PBS and reacted with a solution of avidin in PBS.
3. All other materials are the same as cited in Example I.

Layering of dialysis tubing

1. The Av-membrane is treated with B-RNase dissolved in PBS, and then washed X3 with wash buffer.
2. This B-RNase-coated membrane is treated with avidin in PBS, and then washed X3 with wash buffer, to yield a layer of avidin.
3. Steps 1 and 2 can be repeated in sequence until the desired smaller pore size or other characteristics of the membrane are achieved.

What I claim is:
1. An amidobiotin compound having the formula:

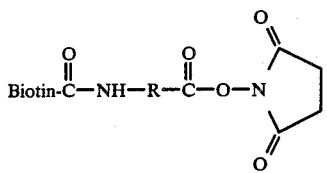

wherein
R is an alkyl group containing 1–12 carbon atoms, a phenylene group, an alkyl-substituent phenylene group, or an alicyclic group containing 5–6 carbon atoms.

2. A compound as recited in claim 1, wherein R is an alkyl group containing 3–10 carbon atoms.

3. A compound as recited in claim 2 wherein R is $(CH_2)_5$.

4. An amidobiotin compound having the formula:

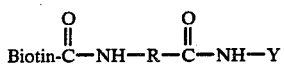

wherein
R is an alkyl group containing 1–12 carbon atoms, a phenylene group, an alkyl-substituted phenylene group, or an alicyclic group containing 5–6 carbon atoms; and
Y is a proteinaceous macromolecule.

5. A compound as recited in claim 4 wherein
R is an alkyl group containing 3–10 carbon atoms; and
Y is an enzyme.

6. A compound as recited in claim 5 wherein
R is $(CH_2)_5$; and
Y is ribonuclease, horseradish peroxidase, or alkaline phosphatase.

7. An amidobiotin compound having the formula:

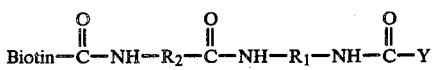

wherein
$R_1$ is an alkyl group containing 2–12 carbon atoms;
$R_2$ is an alkyl group containing 1–12 carbon atoms, a phenylene group, an alkyl-substituted phenylene group, or an alicyclic group containing 5–6 carbon atoms; and
Y is a proteinaceous macromolecule.

8. A compound as recited in claim 7 wherein
$R_1$ is an alkyl group containing 6 carbon atoms;
$R_2$ is an alkyl group containing 3–10 carbon atoms; and
Y is an enzyme.

9. A compound as recited in claim 8 wherein
$R_2$ is $(CH_2)_5$; and
Y is horseradish peroxidase.

* * * * *